United States Patent [19]

Maeda et al.

[11] 4,182,752

[45] Jan. 8, 1980

[54] NEOCARZINOSTATIN DERIVATIVES AND A PROCESS FOR PRODUCING THE SAME

[75] Inventors: Hiroshi Maeda, Kumamoto; Ryunosuke Kanamaru; Nakao Ishida, both of Sendai, all of Japan

[73] Assignee: Kayaku Antibiotic Research Co., Ltd., Tokyo, Japan

[21] Appl. No.: 887,220

[22] Filed: Mar. 16, 1978

[30] Foreign Application Priority Data

Mar. 24, 1977 [JP] Japan ................................ 52-32412

[51] Int. Cl.$^2$ ........................ A61K 31/785; C08F 8/32
[52] U.S. Cl. .............................. 424/78; 260/DIG. 47; 525/328
[58] Field of Search ................. 260/DIG. 47; 526/15; 424/78

[56] References Cited

U.S. PATENT DOCUMENTS

| | | | |
|---|---|---|---|
| 3,121,043 | 2/1964 | Tobin et al. | 526/15 |
| 3,334,022 | 8/1967 | Ishida et al. | 424/116 |

*Primary Examiner*—Stanford M. Levin
*Attorney, Agent, or Firm*—Oblon, Fisher, Spivak, McClelland & Maier

[57] ABSTRACT

Neocarzinostatin derivatives having the formula;

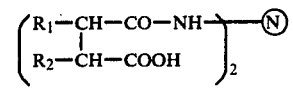

wherein Ⓝ represents a neocarzinostatin residue, and $R_1 + R_2$ represents a residue of polystyrene-maleic acid copolymer having a molecular weight of 2,500 to 80,000. These neocarzinostatin derivatives are prepared by reacting neocarzinostatin with a polystyrene-maleic acid copolymer containing at least one maleic anhydride residue per molecule.

The neocarzinostatin derivatives exhibit anticarcinogenic activity.

3 Claims, 4 Drawing Figures

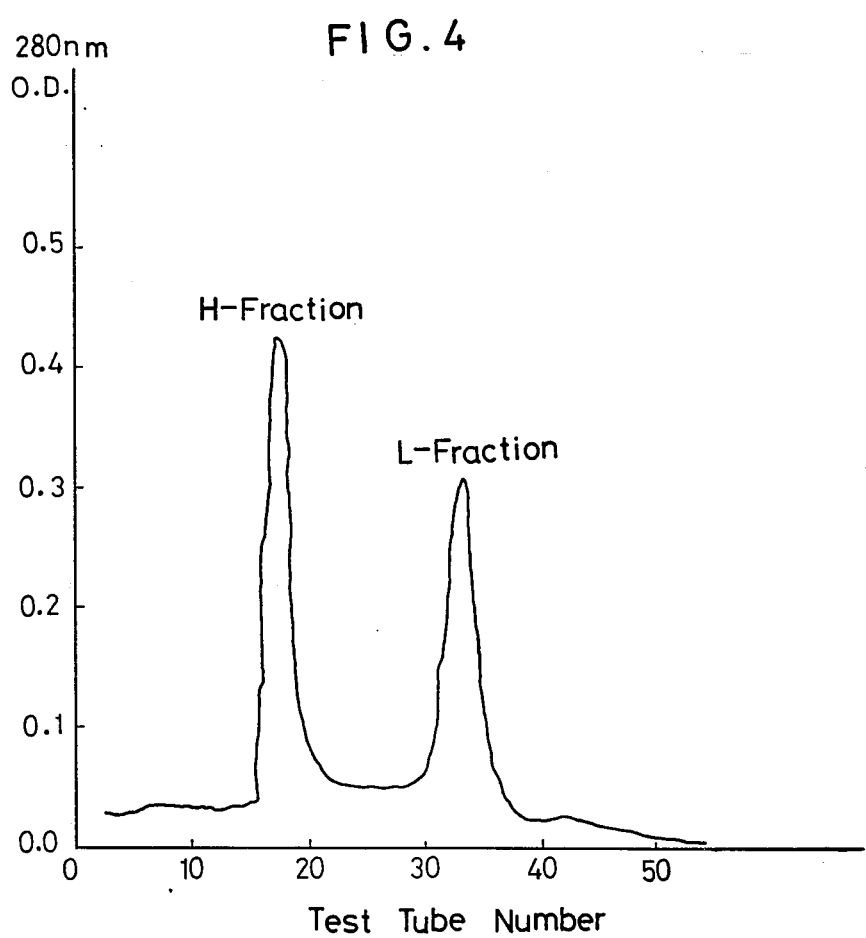

NEOCARZINOSTATIN DERIVATIVES AND A PROCESS FOR PRODUCING THE SAME

BACKGROUND OF THE INVENTION

1. Field of the Invention

This invention relates to novel neocarzinostatin derivatives, more particularly to neocarzinostatin derivatives represented by the formula (I);

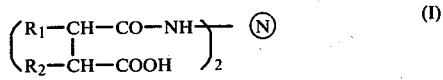

wherein Ⓝ represents a neocarzinostatin residue, and $R_1+R_2$ represents a residue of a polystyrene-maleic acid copolymer having a molecular weight of 2,500 to 80,000, and a process for producing the same.

2. Description of the Prior Art

Neocarzinostatin is a proteinic anticarcinogen produced in a media in which Streptomyces carzinostaticus var. F-41 is cultured (Japanese Patent Publication No. 42(1967)-21752 and U.S. Pat. No. 3,334,022). With respect to the primary structure of this substance, the total number of amino acid residues and estimated molecular weight have been reported to be 109 and 10,700, respectively, by Hiroshi Maeda who is one of the present inventors (Science, 178, 875–876(1972) and Arch. Biochem. Biophys., 163,379–385).

SUMMARY OF THE INVENTION

In the treatment of cancer, the metastasis of cancer cells is important, and the most significant problem is the metastasis of lymphatic glands. A wide variety of neocarzinostatin derivatives have been examined with the aim of lowering the toxicity and prolonging the effects of medicinal values possessed by neocarzinostatin, and with the aim of directing specific migration to the lympho-system. As a result, it was found that the compounds of the formula (I), which are obtained by reacting neocarzinostatin having in its molecule two free amino groups with a water-soluble polystyrene-maleic acid copolymer having a molecular weight of 2,500 to 80,000, possess particularly excellent properties as described above. This invention has been attained based on these findings.

It is, therefore, one object of this invention to provide neocarzinostatin derivatives presenting lower toxicity and specific accumulation in the lympho-system.

It is another object of this invention to provide a novel process for producing the same.

BRIEF DESCRIPTION OF THE DRAWINGS

FIG. 4 shows an elution pattern for the column chromatography of the Example.

DETAILED DESCRIPTION OF THE INVENTION

Figure 1:
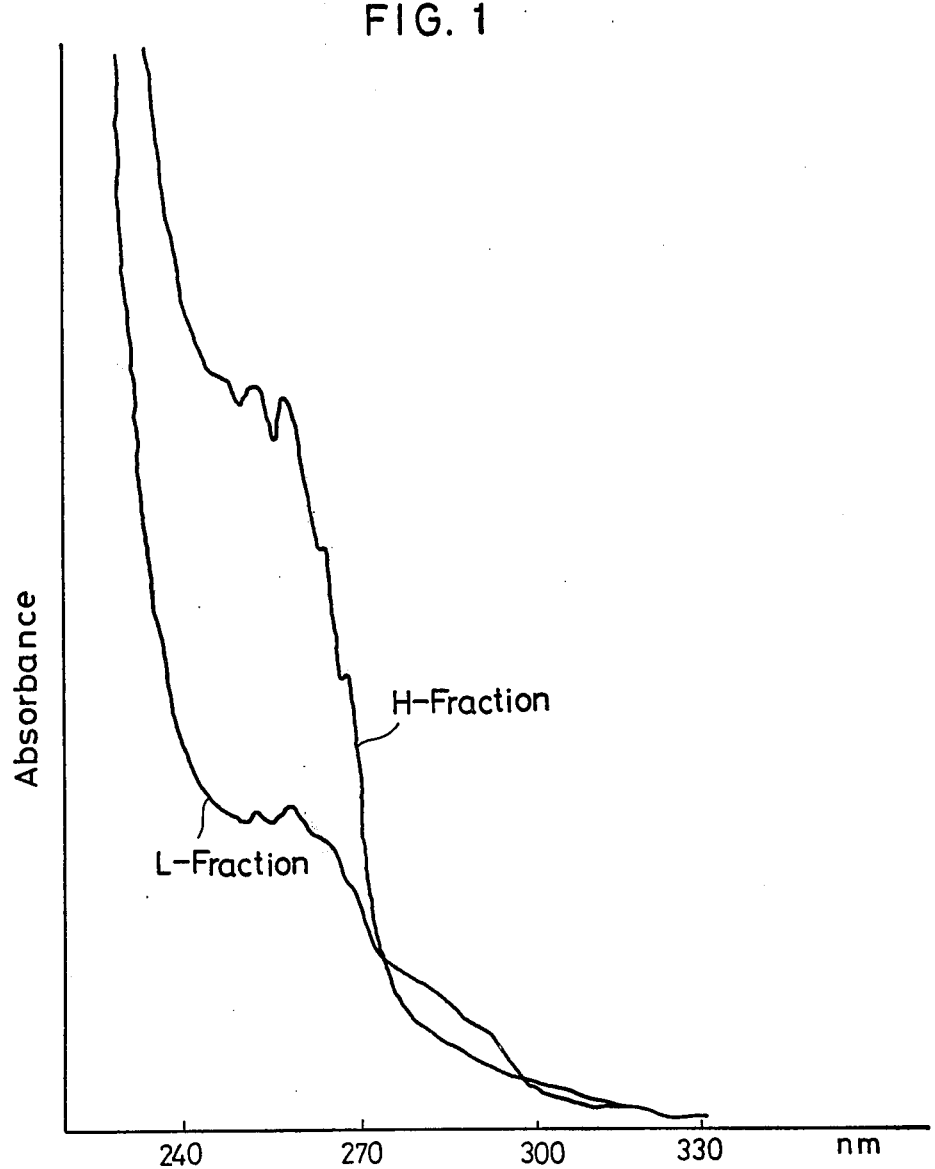
FIG. 1 shows ultraviolet spectra of both the H-fraction and L-fraction of neocarzinostatin derivatives according to the invention.

The neocarzinostatin derivatives of the formula (I) are produced by reacting neocarzinostatin with a polystyrene-maleic acid copolymer containing at least one maleic anhydride residue per molecule.

The polystyrene-maleic acid copolymer has molecular weight in the range of from 2,500 to 80,000 and ranges between 5 to 40 in the degree of polymerization on the basis of maleic acid residues. One of 7 to 8 maleic acid residues should preferably be a maleic anhydride residue.

Reaction of neocarzinostatin with the polystyrene-maleic acid copolymer may be preferably conducted under neutral to weakly basic conditions at a temperature ranging from 0° to 40° C. The two free amino groups of neocarzinostatin are reacted with the maleic anhydride residues of the polystyrene-maleic acid copolymer to yield the compounds of the formula (I).

The biological activities of the thus obtained neocarzinostatin derivatives, fractionated into a high molecular weight fraction (H-fraction) and a low molecular weight are as shown below in terms of their H-fraction having a molecular weight of 150,000 and L-fraction having a molecular weight of 15,000.

| Activities | Minimum effective concentrations | |
|---|---|---|
| | H-Fraction | L-Fraction |
| $R_3HR$-1 cell lymphoblastoid from lymphatic edema) | Less than 2mcg/ml (inhibition of growth) | Less than 1mcg/ml (inhibition of growth) |
| Sarcina lutea | More than 100mcg/ml (anti-bacterial activity) | 2.5mcg/ml (anti-bacterial activity) |
| Acute toxicity in rats | More than 20mg/kg (i.p. maximum tolerance dose) | More than 5mg/kg (i.p. maximum tolerance dose) |
| Inhibition of metastasis of cancer) | Less than 1mg/kg (s.c) | Less than 1mg/kg (s.c.) |
| | (checked by inhibition of metastasis to lymphatic glands after implanting of $10^7$ cells of Yoshida-sarcoma in subcutaneous tissue in rats) | (checked by inhibition of metastasis to lymphatic glands after implanting of $10^7$ cells of Yoshida-sarcoma in subcutaneous tissue in rats) |

As can be seen from the results, the acute toxicities of the intravenous injection of the H- and L-fractions in rats are about 1/50 and about 1/10 in comparison with those of neocarzinostatin. Furthermore, the H- and L-fractions cause an inhibition of the secondary metastasis of AH 109A cancer cells implanted in subcutaneous tissues to lymphatic glands in amounts of only 1/50 and 1/10 respectively of the necessary amount of neocarzinostatin.

The neocarzinostatin derivatives according to the invention can be submitted to practical use as medicaments in human therapy by administration to local tissues, as for example to the primary region of cancer and the cancer-extraction region after operation, or by intracutaneous, subcutaneous, intramuscular, intravenous and oral administration, or by external application, as for example as ointments and suppositories. The dosages depend on administration routes, malignancy degrees of cancer, varieties of cancer, conditions of diseases and general conditions of patients, and advanced degrees of cancer. Further, the dosages depend on the purposes, such as the prevention of metastasis to lymphatic glands after operation, and the medical treatment. The present compounds are preferably administered in a dosage of 0.1 to 10 mg/kg once a day, once or twice a week, or on consecutive days. For local application as ointments or for oral administration, increased dosages are effective.

DETAILED DESCRIPTION OF THE PREFERRED EMBODIMENT

EXAMPLE 1 g of neocarzinostatin was dissolved in 50 ml of a 0.1 M sodium bicarbonate aqueous solution. To the resulting solution was added dropwise with stirring a 35% aqueous solution containing 14 g of a partially hydrolyzed polystyrene-maleic anhydride copolymer, having a molecular weight of 2,500 to 5,000. The mixture thus obtained was reacted at 0° to 40° C. for 60 minutes at an adjusted pH of 7.0 to 9.5. The reaction mixture was dialyzed with distilled water. After removal of the precipitate formed during dialysis with distilled water, the supernatant solution was column-chromatographed on a Sephadex G-100 (1.5×100 cm) column and eluted with a 10 mM ammonium carbonate solution, and there were obtained two fractions as shown in FIG. 4. These fractions were collected, and the higher and lower molecular weight fractions denoted as the H- and L-fractions, respectively. The above-mentioned precipitate exhibited the same biological activities as those shown by the H- and L-fractions.

This biologically active substance was soluble in a 10 mM ammonium carbonate solution.

The properties of the H-fraction and L-fraction are as follows:

(1) Molecular Weight
  H-fraction    about 150,000
  L-fraction    about 15,000
(2) Melting Point
  H-fraction    91°–94° C. (decomposition)
  L-fraction    200°–221° C. (decomposition)
(3) Elemental Analysis

|   | H-fraction | L-fraction |
|---|---|---|
| C | 61.69 | 46.03 |
| H | 7.51 | 7.33 |
| N | 1.70 | 8.18 |

(4) Solubility (Concentration: 2 mg/ml)

|   | H-fraction | L-fraction | Neocarzinostatin |
|---|---|---|---|
| Ethanol | − | − | − |
| Butanol | − | − | − |
| Benzene | ± | ± | − |
| Pyridine | ++ | ++ | − |
| Acetone | − | − | − |

(5) Amino Acid Analysis

About 10 mg of the H-fraction and about 1 mg of the L-fraction were hydrolyzed with 6 N-hydrochloric acid and analyzed. The results obtained are as follows:

|   | H-fraction | L-fraction |
|---|---|---|
| Lysine | 1 | 1 |
| Histidine | 0 | 0 |
| Arginine | 3 | 3 |
| Aspartic acid | 11 | 11 |
| Threonine | 12 | 12 |
| Serine | 10 | 10 |
| Glutamic acid | 5 | 5 |
| Proline | 4 | 4 |
| Glycine | 15 | 15 |
| Alanine | 17 | 17 |
| ½ Cystine | 4 | 4 |
| Valine | 12 | 12 |
| Methionine | 0 | 0 |
| Isoleucine | 1 | 1 |
| Leucine | 6 | 6 |
| Tyrosine | 1 | 1 |
| Phenylalanine | 5 | 5 |
| Tryptophan | 2 | 2 |

(Note 1) The numerical values were calculated using the equation
$$\frac{\text{Number of amino acid residues}}{\text{Average molecular weight}}.$$
(Note 2) As regards tryptophan, the values were determined spectroscopically.

(6) Ultraviolet Absorption Spectra

The H- and L-fractions were dissolved in a 0.15 M ammonium carbonate solution. The results obtained are shown in FIG. 1.

(7) Infrared Absorption Spectra

Figure 2:
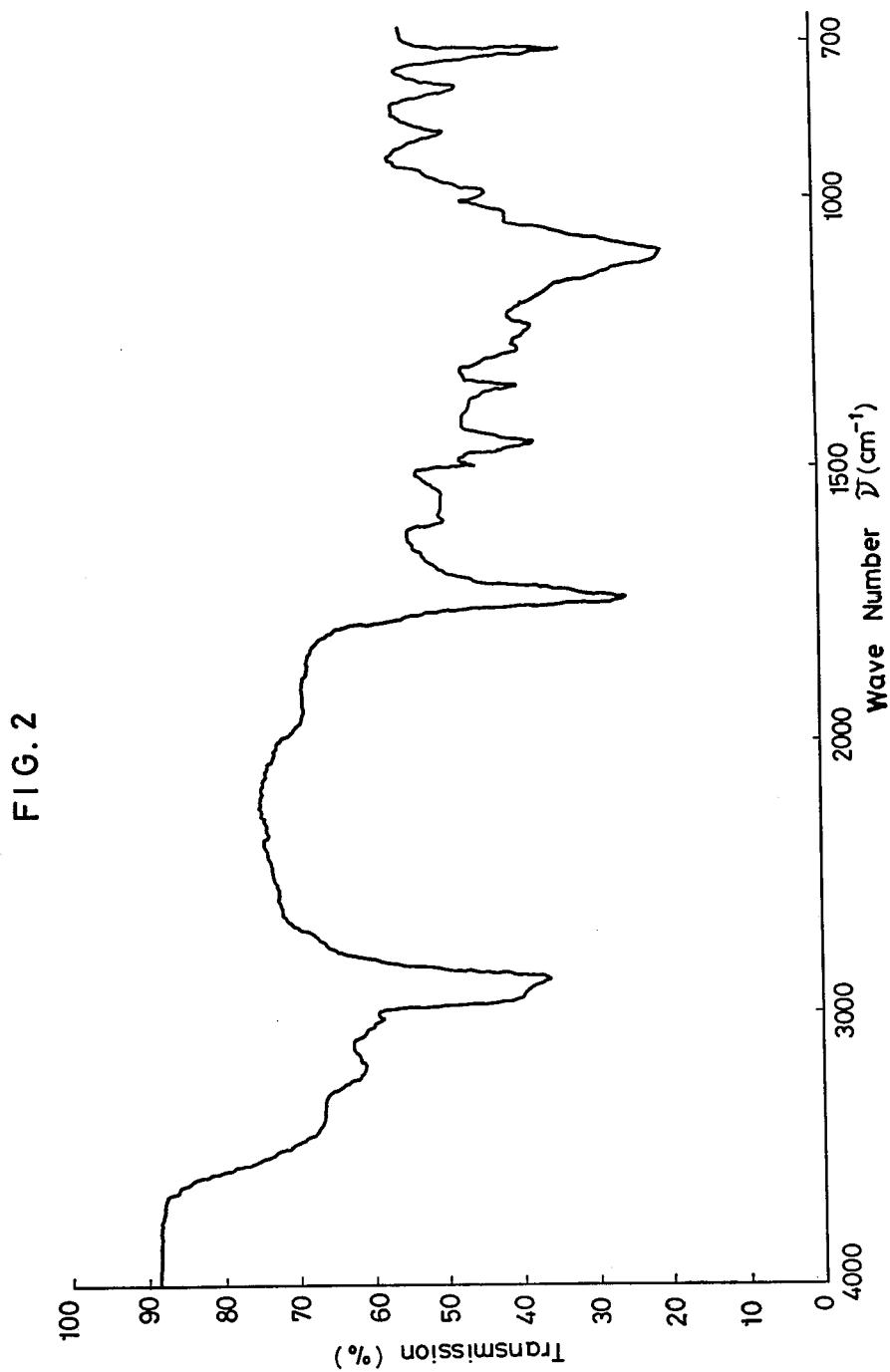
FIG. 2 shows an infrared spectrum of the H-fraction.
Figure 3:
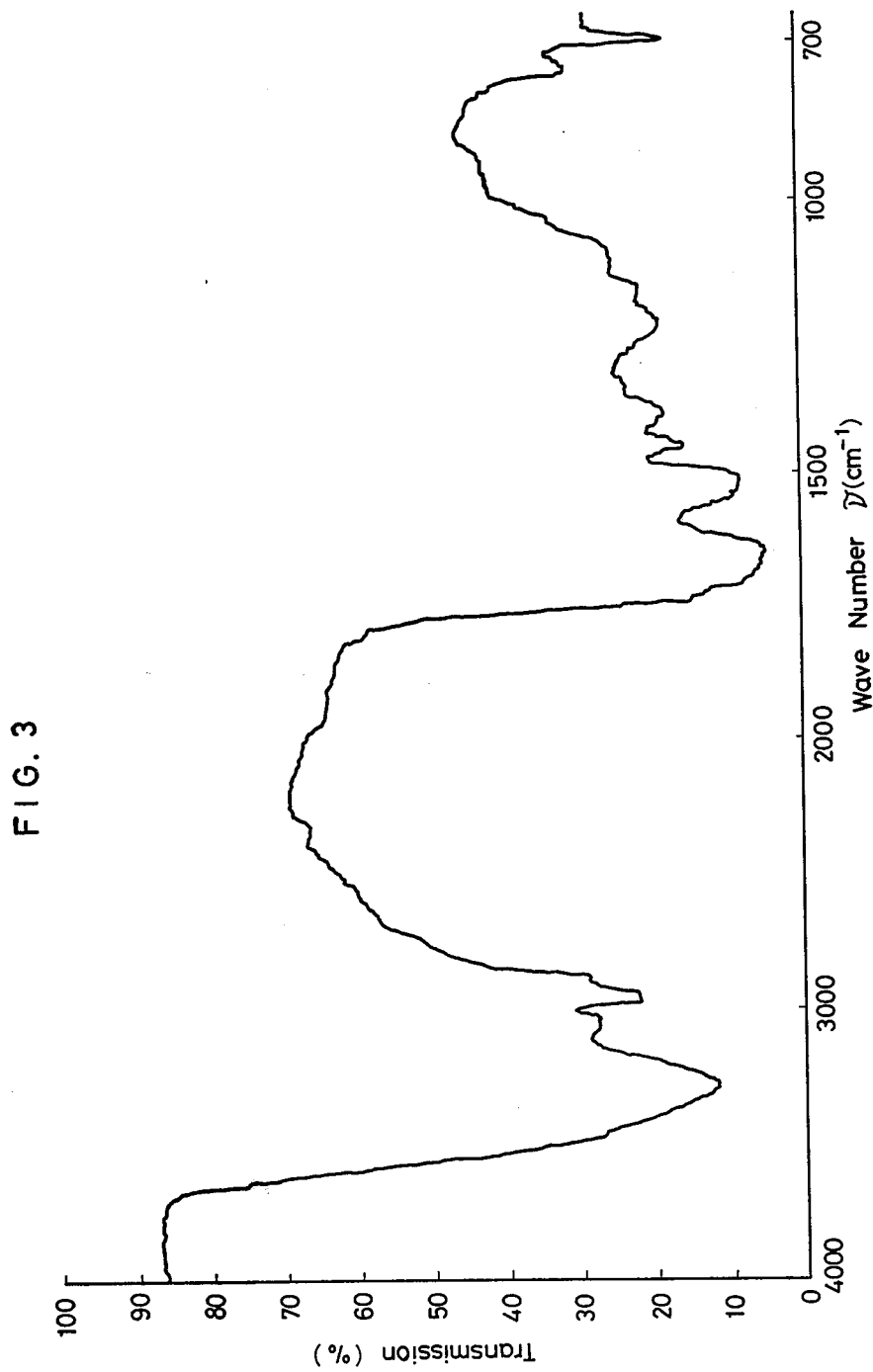
FIG. 3 shows an infrared spectrum of the L-fraction.

The spectra were obtained by the KBr tablet method. FIG. 2 and FIG. 3 show the spectra of the H-fraction and L-fraction, respectively.

What is claimed as new and intended to be covered by Letters Patent is:

1. A neocarzinostatin derivative of the formula:

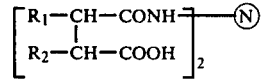

Wherein $\text{N}$ represents a neocarzinostatin nucleus, and $R_1$—CH(CO-)CH(COOH)—$R_2$ represents a polystyrene-maleic acid copolymer, said neocarzinostatin derivative being separable into high and low molecular weight fractions having acute toxicities in rats of about 1/50 and about 1/10 respectively in comparison to neocarzinostatin.

2. A method of inhibiting secondary metastasis of cancer cells which comprises administering an amount effective for said inhibition of the neocarzinostatin derivative of claim 1.

3. The method of claim 2, wherein said effective amount is from 0.1 to 10 mg/kg per administration.

* * * * *